United States Patent
Tomasi et al.

(10) Patent No.: US 6,953,854 B2
(45) Date of Patent: *Oct. 11, 2005

(54) PROCESS FOR PREPARING CRYSTALLINE FORM I OF CABERGOLINE

(75) Inventors: Attilio Tomasi, Milan (IT); Stefania Magenes, Melzo (IT); Mario Ungari, Milan (IT); Giuliano Ramella, Vailate (IT); Gianfranco Pallanza, Milan (IT)

(73) Assignee: Pharmacia, Bury (GB)

( * ) Notice: Subject to any disclaimer, the term of this patent is extended or adjusted under 35 U.S.C. 154(b) by 10 days.

This patent is subject to a terminal disclaimer.

(21) Appl. No.: 10/698,737

(22) Filed: Oct. 31, 2003

(65) Prior Publication Data

US 2004/0092744 A1 May 13, 2004

Related U.S. Application Data

(63) Continuation of application No. 10/239,636, filed as application No. PCT/EP01/03099 on Mar. 19, 2001, now Pat. No. 6,727,363.

(30) Foreign Application Priority Data

Mar. 24, 2000 (GB) ............................................. 0007308

(51) Int. Cl.[7] .................... C07D 457/06; C07D 457/02; A61K 31/48
(52) U.S. Cl. ............................ 546/69; 546/67; 546/61; 514/288
(58) Field of Search ............................ 546/69, 67, 61; 514/288

(56) References Cited

U.S. PATENT DOCUMENTS

| 4,526,892 A | 7/1985 | Salvati et al. |
| 5,382,669 A | 1/1995 | Candiani et al. |
| 5,705,510 A | 1/1998 | Desantis, Jr. |
| 6,727,363 B2 * | 4/2004 | Tomasi et al. ................. 546/69 |
| 2003/0144516 A1 | 7/2003 | Candiani et al. |
| 2003/0149067 A1 | 8/2003 | Tomasi et al. |
| 2003/0187013 A1 | 10/2003 | Tomasi et al. |

FOREIGN PATENT DOCUMENTS

| EP | 0040325 B1 | 3/1986 |
| GB | 2103603 A | 2/1983 |
| WO | WO 95/05176 A1 | 2/1995 |
| WO | WO 99/36095 A1 | 7/1999 |
| WO | WO 99/48484 A2 | 9/1999 |
| WO | WO 01/70740 A1 | 9/2001 |

OTHER PUBLICATIONS

P. Sabatino et al, "X–ray Crystal Structure and Conformational Analysis of N– (3–diamethylaminopropyl) N– ethlaminocarbonyl– 6– (2– propenyl) ergoline– 8–beta–carboxamide (cabergoline)", II Farmco, vol. 50—No. 3, pp. 175–178, 1995.

E. Brambilla et al, "Synthesis and Nidtion Activity of a New Class of Ergoline Derivative", European Journal of Medicinal Chemistry, vol. 24, pp. 421–426, 1989.

International Search Report, 3 pages, (Aug. 2001).

* cited by examiner

*Primary Examiner*—Charanjit S. Aulakh
(74) *Attorney, Agent, or Firm*—Akin Gump Strauss Hauer & Feld LLP

(57) ABSTRACT

A process for producing crystalline form I of cabergoline, which process comprises crystallization of the desired form from a toluene/diethyl ether mixture comprising raw cabergoline, followed by recovery and drying of the resulting crystals. A new solvate form V of cabergoline, useful as an intermediate, is also provided.

8 Claims, 8 Drawing Sheets

US 6,953,854 B2

PROCESS FOR PREPARING CRYSTALLINE FORM I OF CABERGOLINE

CROSS-REFERENCE TO RELATED APPLICATIONS

This application is a continuation of U.S. application Ser. No. 10/239,636 filed Feb. 3, 2003 now U.S. Pat. No 6,727,363 which in turn was a 371 of PCT/EP01/03099 filed Mar. 19, 2001 which in turn claimed priority through GB 0007308.0 filed Mar. 24, 2000.

STATEMENTS REGARDING FEDERALLY SPONSORED RESEARCH OR DEVELOPMENT

Not applicable.

REFERENCE TO A MICROFICHE APPENDIX

Not applicable.

BACKGROUND OF THE INVENTION

1. Field of the Invention

The present invention concerns a new process for preparing crystalline Form I of cabergoline.

2. Description of the Related Art

Cabergoline is an ergoline derivative interacting with D2 dopamine receptors and is endowed with different useful pharmaceutical activities and it is used in the treatment of hyperprolactinemia, central nervous system disorders (CNS) and other related diseases.

Cabergoline is the generic name of 1((6-allylergolin-8beta-yl)-carbonyl)-1-(3-dimethylaminopropyl)-3-ethylurea, decribed and claimed in U.S. Pat. No. 4,526,892. The synthesis of cabergoline molecule is reported also in Eur. J. Med. Chem., 24,421, (1989) and in GB 2,103,603. Crystalline cabergoline Form I, an anhydrous not solvated form of cabergoline, was prepared by crystallization from diethyl ether, as described in Il Farmaco, 50 (3), 175–178 (1995).

Cabergoline Form I, like cabergoline, displays a significant inhibitory effect with regard prolactine and has therapeutic properties that make it possible to treat patients who have pathological conditions associated with an abnormal prolactin level, thus is useful in human and/or veterinary medicine. Cabergoline is also active, alone or in combination, in the treatment of reversible obstructive airways diseases, for controlling intraocular pressure and for the treatment of glaucoma. It is also employed in the veterinary field, as antiprolactin agent and in cutting down drastically the proliferation of vertebrate animals. The several uses of cabergoline are for example described in WO 99/48484, WO 99/36095, U.S. Pat No. 5,705,510, WO 95/05176, EP 0 040 325.

Cabergoline Form I is particularly useful in the treatment of Parkinson's disease (PD), Restless Legs Syndrome (RLS), treatment of diseases like Progressive Supranuclear Palsy (PSP) and Multysystemic atrophy (MSA).

BRIEF SUMMARY OF THE INVENTION

During our development work we discovered a new process for preparing crystalline Form I.

Thus, the present invention concerns a new process for preparing Form I of cabergoline and a new solvate Form V of cabergoline useful as intermediate.

DETAILED DESCRIPTION OF THE INVENTION

Form I can be readily prepared according to the present invention starting from crude material by crystallization from a toluene/diethyl ether mixture, through a new solvate form V of cabergoline. The present process for preparing Form I shows advantages with respect to the old one because of its greater reproducibility.

Characterisation

X-ray powder diffraction (XRD), differential scanning calorimetry (DSC), infrared (IR) spectroscopy and solid state C-NMR were used to characterise the new form.

X-Ray Powder Diffraction

Powder X-ray diffraction was performed using either a Scintag X1 or X2 Advanced Diffraction System operating under Scintag DMS/NT(c) Ver 1.30a and 1.36b respectively, and Microsoft Windows NT 4.0(™) software. The system used a copper X-ray source maintained at 45 kV and 40 mA to provide CuK[alpha] emission of 1.5406 Angstroms and a solid state peltier cooled detector. Beam aperture was controlled using tube divergence and anti-scatter slits of 2 and 4 mm and detector anti-scatter and receiving slits of 0.5 and 0.3 mm width. Data were collected from 2[deg.] to 30[deg.] two-theta using a step scan of 0.03[deg.]/point with a one second/point counting time. The samples were hand ground using a pestle and mortar and packed into an aluminum sample tray with a 12 mm (diam.)*0.5 mm cavity.

DSC

Measurements of differential scanning calorimetry were obtained on a Mettler TA 4000 thermal analysis system. Approximately 8.5 mg samples were accurately weighed into a DSC pan. The pans were hermetically sealed and a pinhole was punched into the pan lid. The use of the pinhole allows for pressure release, but still assures that the thermal reactions proceed under controlled conditions. The samples were introduced into the DSC oven and then heated at a rate of 5[deg.] C./min, up to a final temperature of 135[deg.] C.

IR Spectroscopy

IR spectra of cabergoline form I and V were obtained on a Perkin Elmer FT-IR spectrophotometer PARAGON 1000. The sample were prepared by KBr powder technique registering the spectra on reflectance.

Solid State C-NMR

Figure 1:
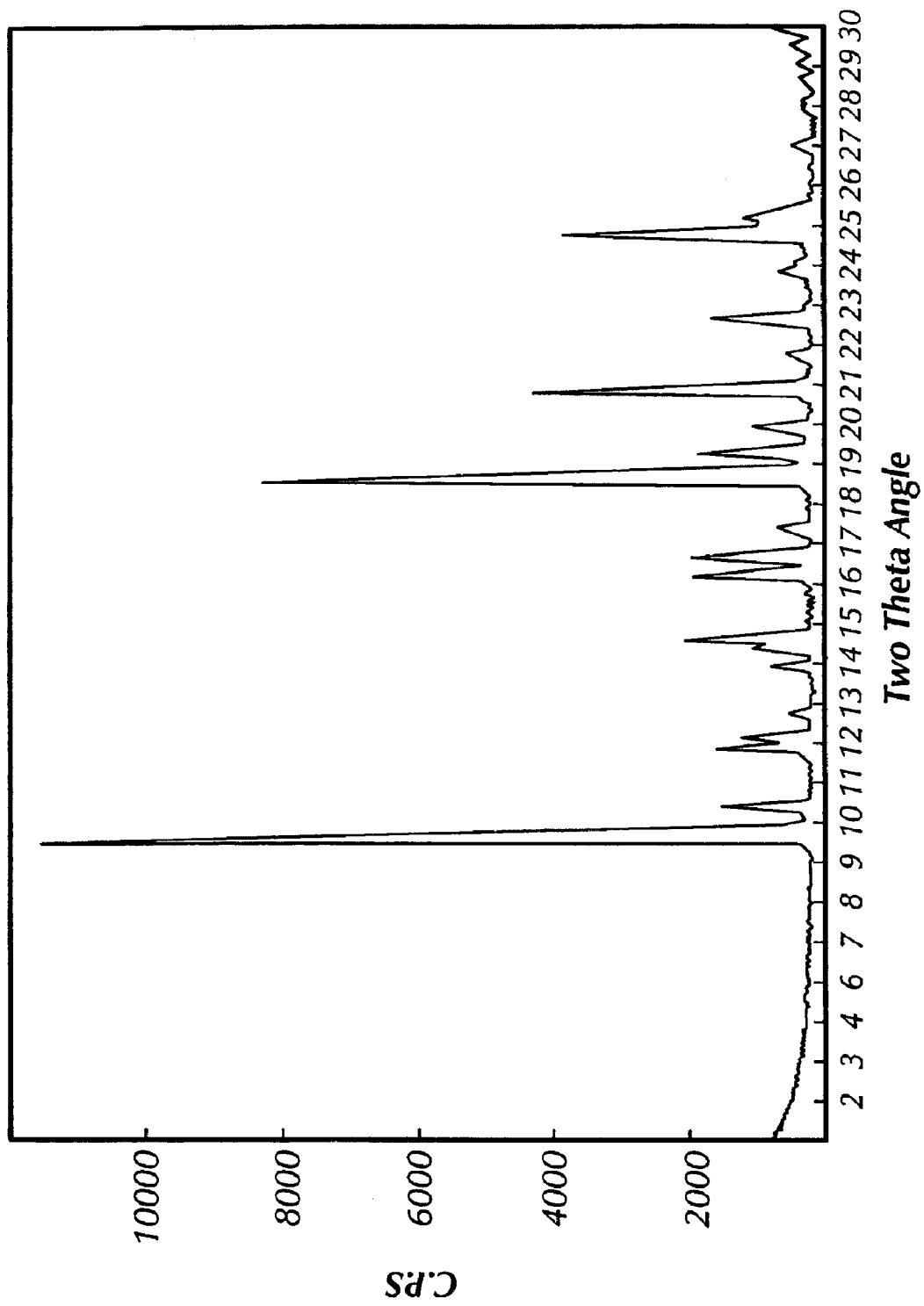
FIG. 1. XRD powder pattern of cabergoline Form I.
Figure 2:
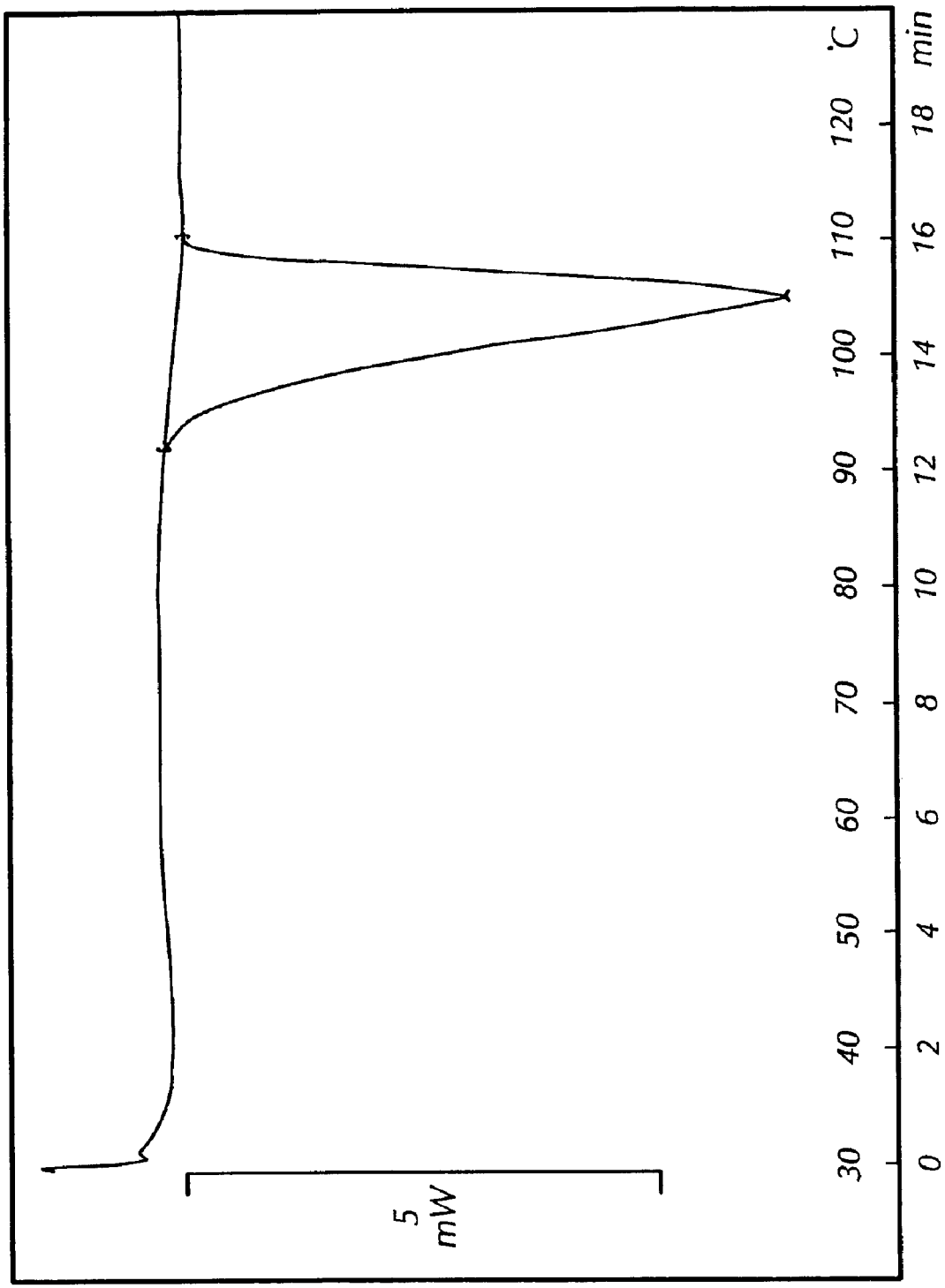
FIG. 2. DSC curve of cabergoline Form I.

Solid state C-NMR spectra were obtained on a MSL 300 Bruker instrument equipped with solid state facilities and variable temperature magic angle spinning probe. Cross polarisation experiments were performed by a decoupling field of 50 KHz and single pulse magic angle spinning experiments with recycle times ranging from 10 to 100 records. The x-ray powder diffraction pattern for Form I (FIG. 1) shows a crystalline structure with useful distinctive peaks at approximately 9.7, 10.4 and 24.8 deg 2-theta. The DSC curve of Form I (FIG. 2) exhibits a melting endotherm at approximately 100[deg.]–105[deg.] C. The integrated melting endotherm has a heat of fusion of approximately 60 J/g.

Figure 3:
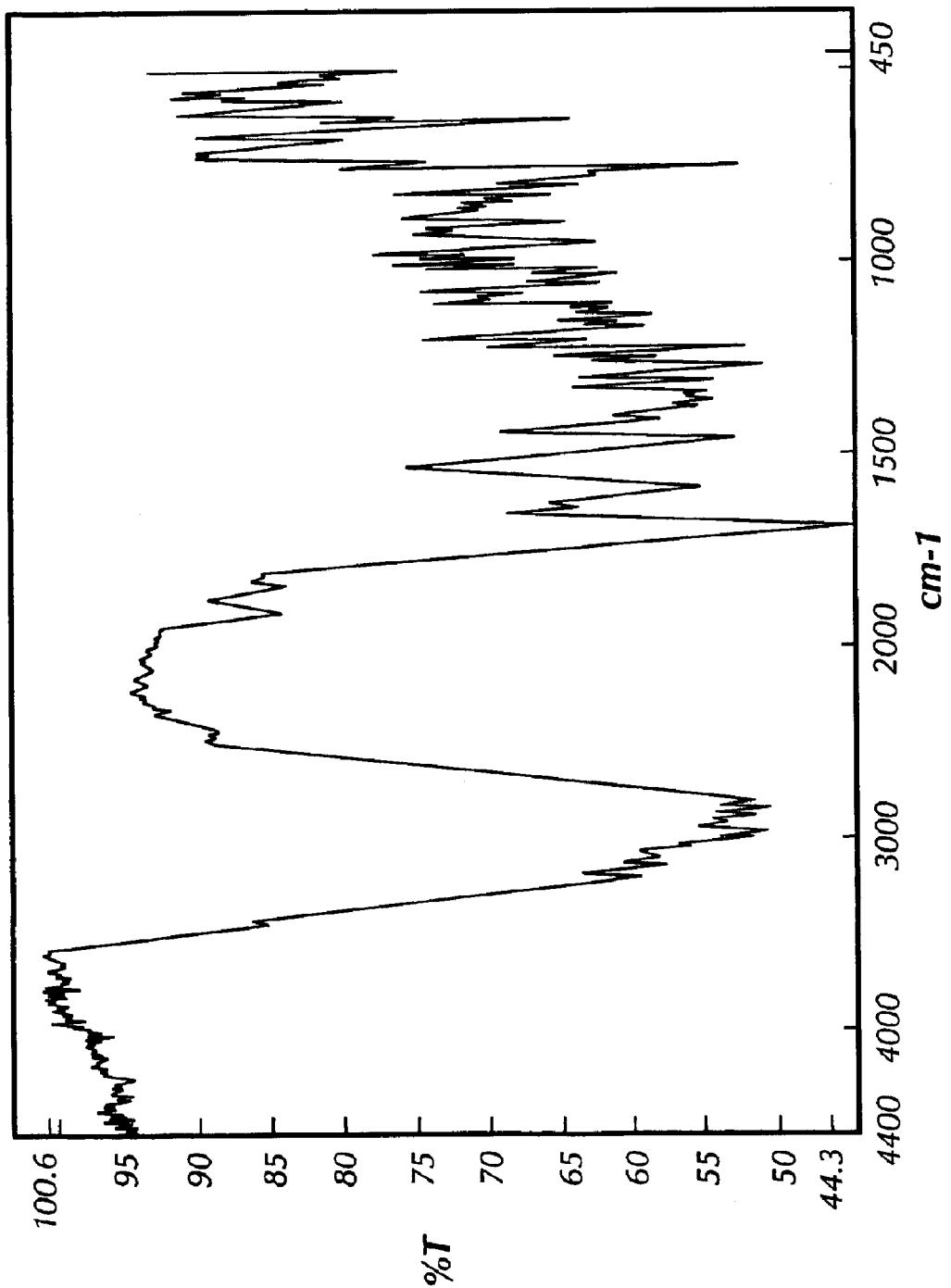
FIG. 3. IR spectrum of cabergoline Form I (sample prepared by KBr powder technique).

The IR spectrum of Form I is shown in FIG. 3.

Figure 4:
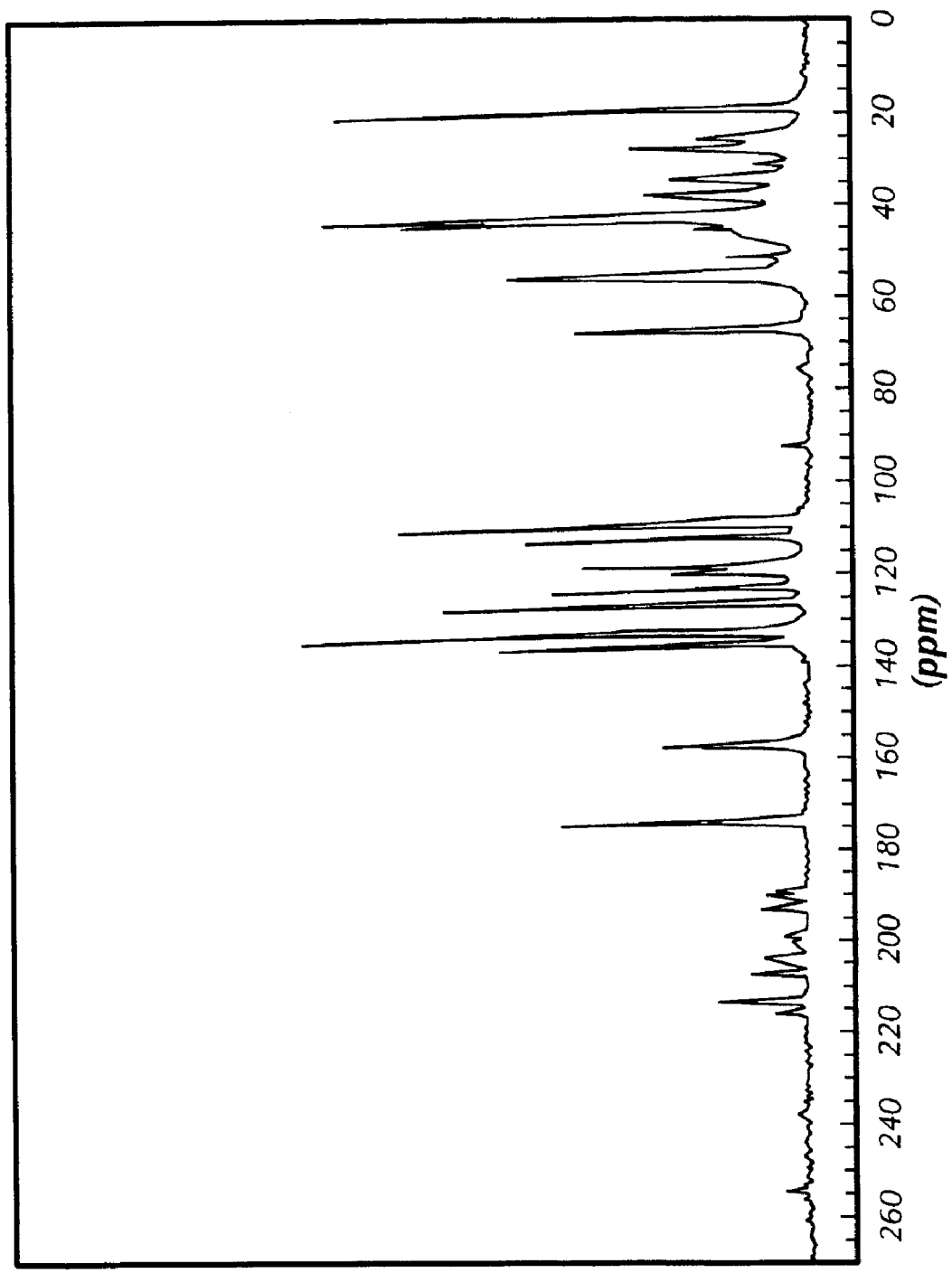
FIG. 4. Solid state C-NMR spectrum of cabergoline form I.

The solid state C-NMR spectrum of form I is shown in FIG. 4.

Figure 5:
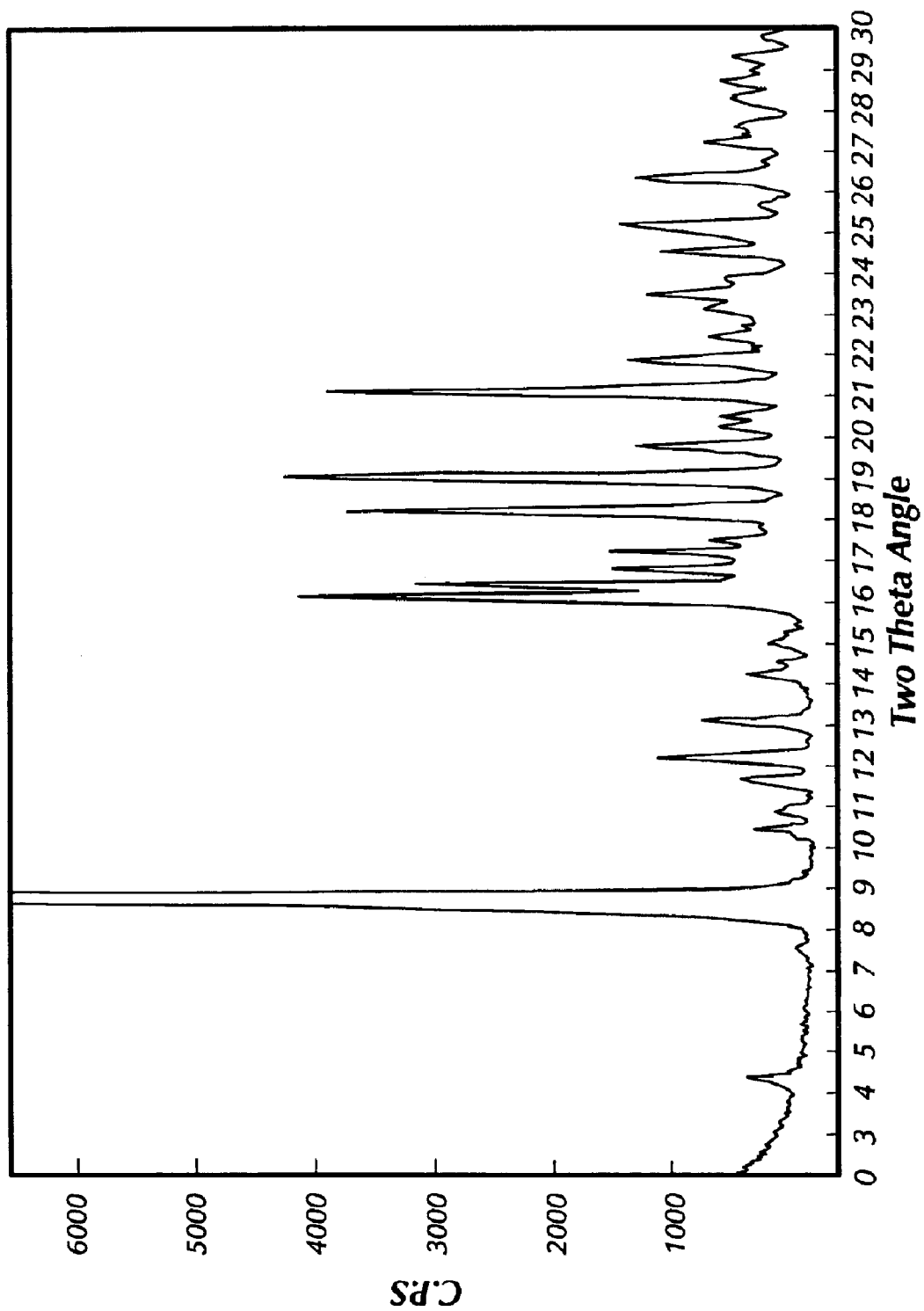
FIG. 5. XRD powder pattern of cabergoline solvate Form V.

These data indicate that cabergoline Form I is a crystalline polymorph easily distinguishable by XRD and solid state C-NMR techniques. DSC and IR are other two useful techniques to characterize the polymorph. The process of the present invention for producing crystalline cabergoline Form I is characterized by crystallisation from a toluene/diethyl ether mixture. The process comprises dissolving the raw final cabergoline, obtained as an oil through the synthesis described in Eur. J. Med. Chem., 24, 421, (1989), in a suitable amount of a toluene/diethyl ether mixture, preferably about 1:1 mixture. The resultant solution is then cooled at a temperature of from −25[deg.] to −9[deg.] C., preferably at about −12[deg.] C. for 17 hours. In these conditions, a toluene solvate is obtained, named Form V, that may be recovered by common procedures, for example by filtration under reduced pressure or by centrifugal filtration, followed by smoothly drying of the resultant solid. The resultant crystals of Form V are then converted into form I upon further drying. The crystals of Form I of cabergoline prepared according to the process of the present invention have preferably a polymorph purity >95%, more preferably >98%. Toluene solvate form V is also object of the present invention. The x-ray powder diffraction pattern for Form V (FIG. 5) shows a crystalline structure.

Figure 6:
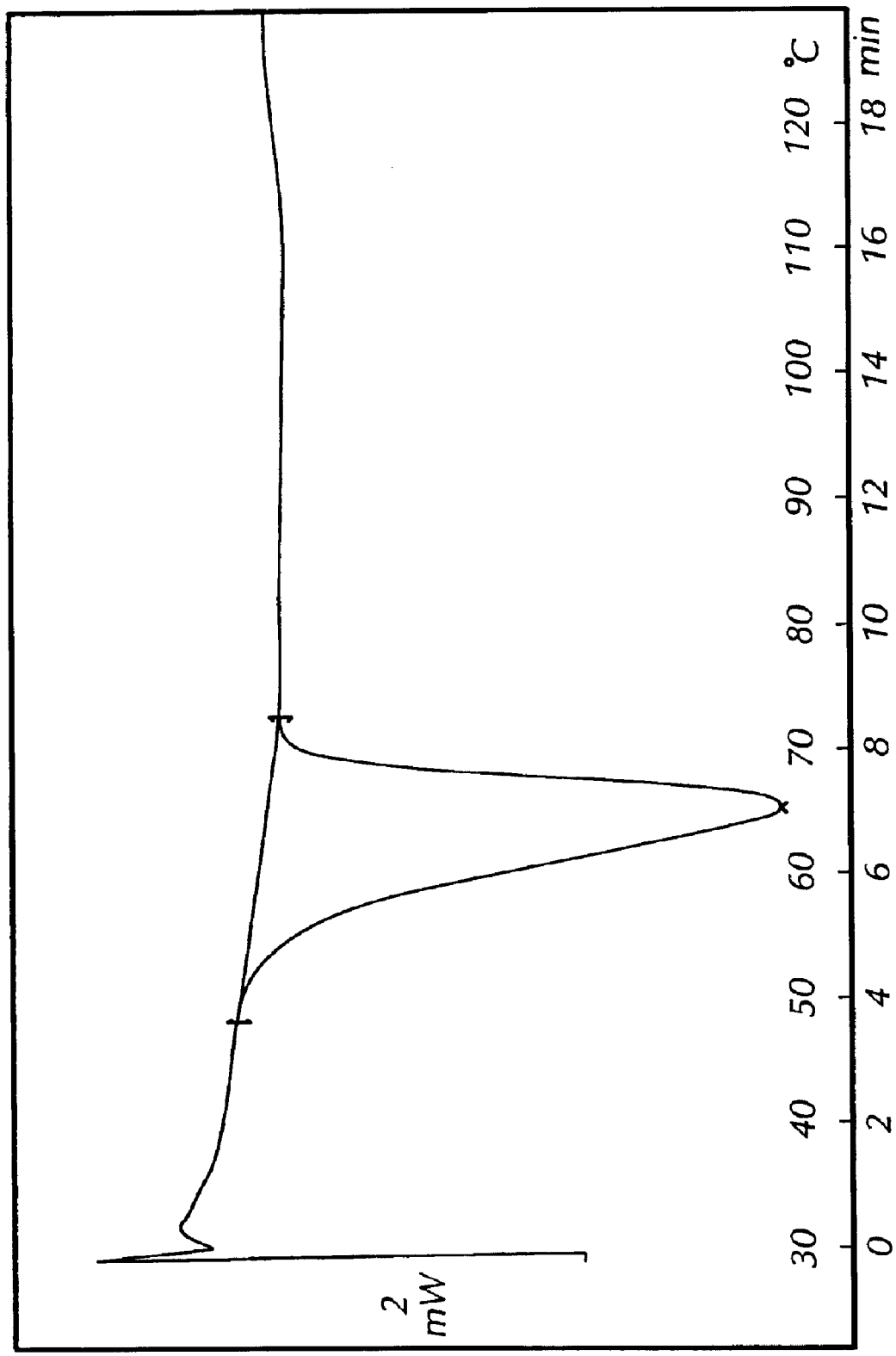
FIG. 6. DSC curve of cabergoline solvate Form V.

The DSC curve of solvate Form V (FIG. 6) exhibits a melting endotherm at approximately 60[deg.]–65[deg.] C.

Figure 7:
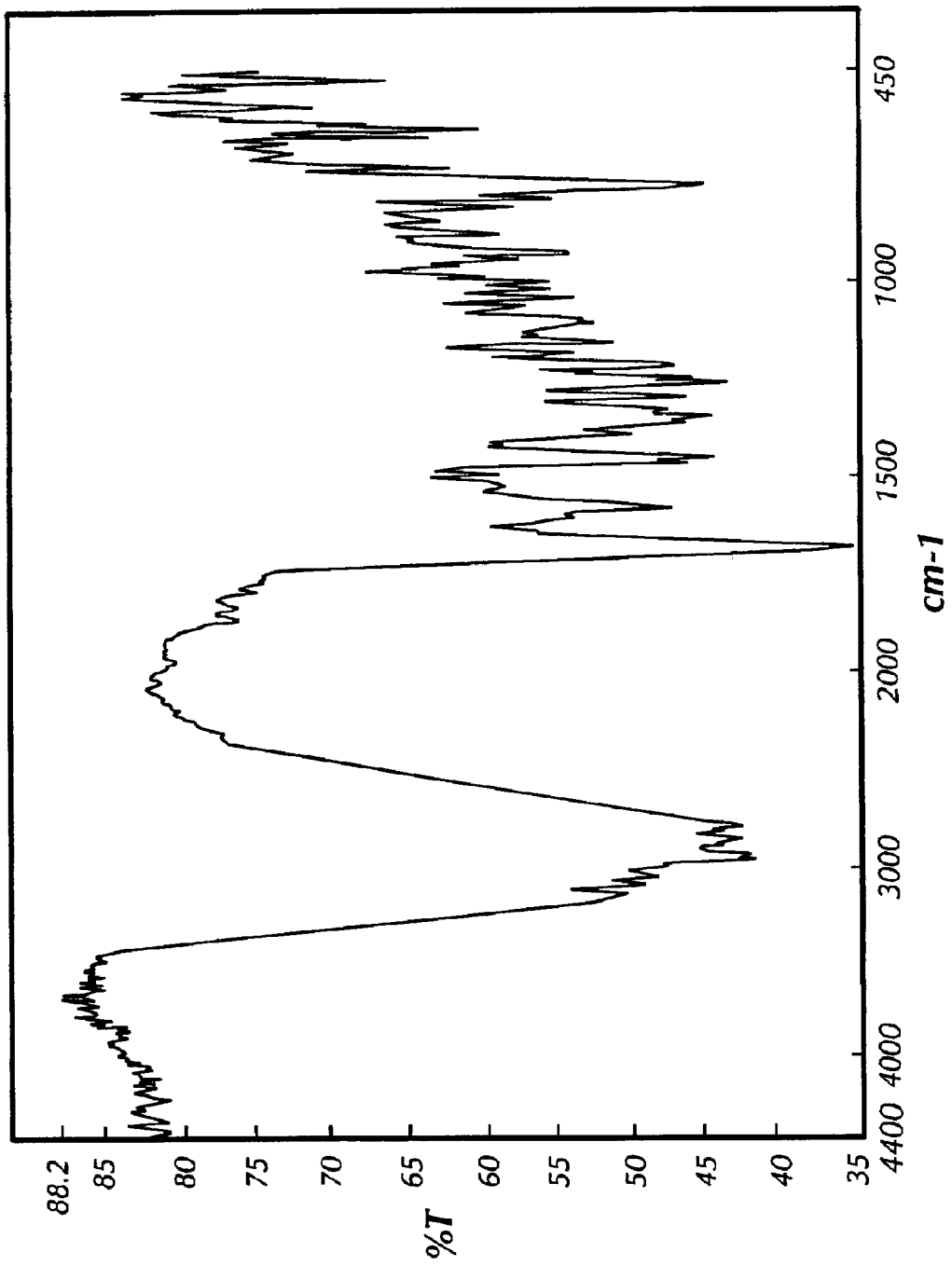
FIG. 7. IR spectrum of cabergoline solvate Form V (sample prepared by KBr powder technique).
Figure 8:
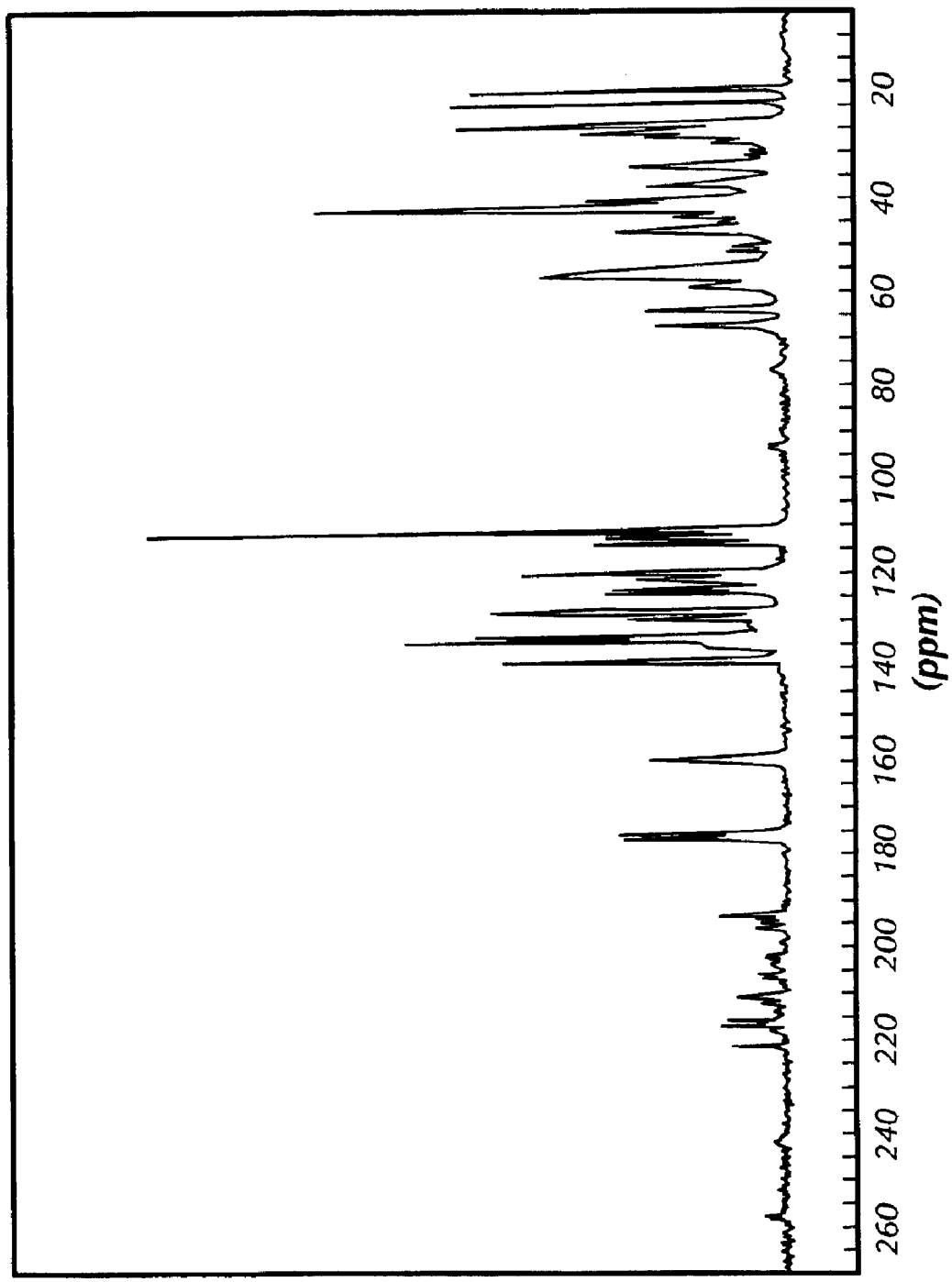
FIG. 8. Solid state C-NMR spectrum of cabergoline solvate Form V.

The IR spectrum of solvate Form V is shown in FIG. 7. The solid state C-NMR spectrum of form V is shown in FIG. 8.

These data indicate that cabergoline solvate Form V is easily distinguishable by XRD, DSC and solid state C-NMR techniques. IR, combined with another analytical technique, is another method to identify the solvate.

The solvate V of this invention is a true solvate having a fixed composition of about 0.5 toluene moles per mole of cabergoline.

EXAMPLE 1

The oil obtained by purification on a chromatographic column after the final step of the synthetic path according to the preparation described in Eur. J. Med. Chem., 24, 421, (1989) and containing 100 g of pure cabergoline was dissolved in toluene to give 243 g of a cabergoline toluene solution. The solution was introduced into a reactor pre-cooled at −12[deg.] C., and 182 g of toluene were added to give a 23.5%. w/w cabergoline concentration in this solvent. After cooling again at −12[deg.] C., 362 ml of diethyl ether were added. The mixture was cooled again at −12[deg.] C. and stirred at this temperature for about 17 hours. The obtained precipitate was filtered under vacuum and smoothly dried. The resultant crystal solvate form V was identified by XRD, DSC, IR and NMR, data shown in FIGS. 5–8 respectively.

Yield was about 45% (w/w) on the basis of pure cabergoline initial content.

EXAMPLE 2

The crystal solvate form V obtained in example 1 was dried at a temperature of from 40[deg.] C. under vacuum to 65[deg.] C. under vacuum. After drying, the resultant crystal form I was identified by XRD, DSC, IR and NMR, data shown in FIGS. 1–4 respectively. Yield was about 40% on the basis of pure cabergoline initial content. The assayed polymorph purity was >98%.

We claim:

1. A process for producing crystalline Form I of cabergoline with a purity >95%, which process comprises crystallisation of raw cabergoline from a toluene/diethyl ether mixture, through a solvate form V of cabergoline.

2. A process according to claim 1 in which the crystallization comprises dissolving raw cabergoline in a toluene/diethyl ether mixture, cooling the resulting solution, collecting the resulting solvate form V of cabergoline having the XRD powder pattern of FIG. 5 and converting the solvate into cabergoline Form I by drying.

3. A process according to claim 1 or 2 in which the toluene/diethyl ether mixture is a 1:1 mixture.

4. A process according to claim 2 in which the toluene/diethyl ether mixture is cooled to a temperature of from −25° to −9° C.

5. A process according to claim 3 in which the toluene/diethyl ether mixture is cooled to a temperature of from −25° to −9° C.

6. A process according to claim 4, in which the toluene/diethyl ether mixture is cooled to a temperature of about −12° C.

7. A process according to claim 5, in which the toluene/diethyl ether mixture is cooled to a temperature of about −12° C.

8. A process for producing crystalline Form I of cabergoline with a purity >95% having an XRD powder pattern exhibiting peaks at approximately 9.7, 10.4 and 24.8 deg 2-theta, which process comprises crystallisation of raw cabergoline from a toluene/diethyl ether mixture, through a solvate form V of cabergoline having an XRD powder pattern exhibiting peaks at approximately 8.6, 16.0, 18.1, 18.9 and 20.9 deg 2-theta.

* * * * *